United States Patent [19]
Dozono

[11] Patent Number: 5,262,161
[45] Date of Patent: * Nov. 16, 1993

[54] STEVIA EXTRACT-CONTAINING MEDICINE

[75] Inventor: Fumio Dozono, 3040, Oaza-Homanbo, Takajo-cho, Kitamorokata-gun, Miyazaki-ken, Japan

[73] Assignees: Fumio Dozono, Miyazaki; Naohiko Sato, Tokyo, both of Japan

[*] Notice: The portion of the term of this patent subsequent to Oct. 5, 2010 has been disclaimed.

[21] Appl. No.: 769,037

[22] Filed: Sep. 30, 1991

[51] Int. Cl.$^5$ .............................................. A61K 35/78
[52] U.S. Cl. .................. 424/195.1; 514/814; 514/825; 514/829; 514/859; 514/861; 514/862; 514/865; 514/886; 514/887; 514/852
[58] Field of Search ............... 424/195.1; 514/814, 514/825, 861, 859, 887, 886, 829, 852, 858, 882

[56] References Cited

FOREIGN PATENT DOCUMENTS 3-127959  5/1991  Japan .
3-151321  6/1991  Japan .
3-220109  9/1991  Japan .
4-66535   3/1992  Japan .

*Primary Examiner*—John W. Rollins
*Attorney, Agent, or Firm*—Jordan and Hamburg

[57] ABSTRACT

A medicine for skin diseases contains a fermented and condensed extract from the stems of *Stevia Rebaudiana Bertoni* as an active ingredient. The medicine is prepared by condensing and fermenting an extract from the ripened stems of *Stevia Rebaudiana Bertoni* by multi-stage condensation followed by fermentation and ripening of the condensed extract. It is effective for various skin diseases and other diseases caused by blood circulation insufficiency.

13 Claims, No Drawings

STEVIA EXTRACT-CONTAINING MEDICINE

BACKGROUND OF THE INVENTION

The present invention relates to a medicine for the treatment of skin diseases and a method of preparing them. More precisely, it relates to a medicine for skin diseases obtained by fermentation of an extract from stems of an herb plant *Stevia Rebaudiana Bertoni* (botanical name), as well as to a method of preparing them.

It has been well known prior to the filing date of the application of the present invention that an extract from *Stevia Rebaudiana Bertoni* is usable as a sweetener.

The present inventor has participated in studies of extracts from *Stevia Rebaudiana Bertoni* for many years. For instance, he completed a method of preparing a sweetener by ripening a condensed liquid as extracted from leaves of *Stevia Rebaudiana Bertoni* by a particular means (Japanese Published Kokai No. 1-127959); a horticultural manure obtained by fermenting an extract from a mixture of leaves and stems of *Stevia Rebaudiana Bertoni* and a method of preparing the same (Japanese Published Kokai No. 3-220109); and a bathing aid obtained by fermenting an extract from the stems of *Stevia Rebaudiana Bertoni* and a method of preparing the same (Japanese Published Kokai No. 3-151321), filing The present inventor traced the above-mentioned inventions and further studied them, whereupon he has found that the substance obtained by fermenting an extract from stems of *Stevia Rebaudiana Bertoni* has an excellent blood circulation promoting property and is useful as a medicine for skin diseases. He has now completed the present invention.

SUMMARY OF THE INVENTION

The object of the present invention is to provide a medicine for skin diseases, containing only one natural component and not containing any other synthetic chemicals, which displays an excellent pharmaceutical effect.

Another object of the present invention is to provide a method for preparing such a medicine for skin diseases.

In order to attain the objects, there is provided, in accordance with the present invention, a medicine for skin diseases containing a fermented condensed liquid from stems of *Stevia Rebaudiana Bertoni*.

There is also provided, in accordance with the present invention, a method for preparing such a medicine for skin diseases by fermenting an extract from stems of *Stevia Rebaudiana Bertoni*.

DESCRIPTION OF THE PREFERRED EMBODIMENTS OF THE INVENTION

The most important technical characteristic of the present invention resides in the use of a product to be obtained by fermenting an extract from only the stems of *Stevia Rebaudiana Bertoni* as a medicine for skin diseases.

As a result of studies by the present inventor, it has been found that the stems of *Stevia Rebaudiana Bertoni* contain microorganisms which are not in the leaves of the same plant. Furthermore, a product obtained by drying, powdering and boiling the stems to provide a condensed extract followed by fermentation of the extract, preferably in a closed tank under heat, has an excellent blood circulation promoting property and additionally displays a pharmaceutical effect as a medicine for skin diseases.

The medicine for skin diseases of the present invention is to be applied to the diseased part of the skin whereby the blood circulation of the topical area is promoted and the disease is healed.

Another characteristic aspect of the present invention is that ripened stems of *Stevia Rebaudiana Bertoni* are used as the raw material for the medicine.

*Stevia Rebaudiana Bertoni* is a perennial plant of the family Compositae (Asteraceae), which is native to the South American countries of Paraguay and Brazil. For cultivating the plant, seedlings or cuttings thereof are generally implanted around April or May, and young leaves from the grown plants are harvested two or three times a year.

However, such young leaves and young plants of *Stevia Rebaudiana Bertoni* are not suitable for use in the present invention, as they lack a sufficient pharmaceutical effect. Therefore, this invention requires that the ripened plants of *Stevia Rebaudiana Bertoni* are harvested only once a year around October or November and that the stems of the harvested plants are used in the present invention. The harvested plants are dried at about 70° to 80° C. for roughly 24 hours and divided into their leaves, stems and branches. Only the stems are ground into a size of 15 $\mu$ or less, preferably approximately from 1 to 8 $\mu$, and the thus ground substance is boiled for extraction. The leaves of *Stevia Rebaudiana Bertoni* contain components for a sweetener but do not contain components that display a pharmaceutical effect as a medicine for skin diseases, and therefore they are not suitable for the present invention.

The extract thus obtained from the stems of ripened *Stevia Rebaudiana Bertoni* is then condensed and fermented, for example, as mentioned below.

(1) Six liters of water are put in an iron container and heated. At boiling, the heat is discontinued, and 1 kg of a mixed powder comprised of dried and ground stems of *Stevia Rebaudiana Bertoni* is gently added thereto with stirring. Heating is re-continued and the content is boiled down and stirred for one hour.

(2) The thus boiled down material is filtered under suction with a squeezer to separate the liquid component from the refuse. The thus obtained first condensed liquid (3 to 4 liters) is stored in a tank (condensing reactor).

(3) Next, about 4 liters of water is added to the above-mentioned iron container and heated. At boiling, the heat is discontinued, and the above-mentioned first refuse is added thereto. With heat, the content in the container is then boiled down for about one hour.

(4) The thus boiled down material is filtered under suction with a squeezer to separate the liquid component from the refuse. The amount of the thus obtained second condensed liquid is about 3 liters.

(5) The second condensed liquid is added to the tank (condensing reactor) which already contains the first condensed liquid, and mixed. The resulting mixture is boiled down with heat for about 3 to 4 hours. After the amount of the condensed mixture liquid has been reduced to about one liter by boiling, the condensation step is finished.

(6) The thus obtained condensed liquid is filtered, and the resulting filtrate is put in a storage tank, which is stored for long fermentation under the conditions of 15° to 30° C., preferably 15° to 25° C., for 90 to 360 days, preferably 180 to 360 days.

In accordance with the present invention, the condensation of the extract is preferably implemented by a multi-stage condensation method comprising two or more condensation steps, whereby more effective extraction is attained. However, four or more condensation steps would be meaningless in view of the condensation of the extract to be obtained and, as such, would be economically disadvantageous.

The medicine for skin diseases of the present invention thus obtained is generally diluted with water to a ½ to 1/5 concentration, preferably to a ¼ to ⅓ concentration. The thus diluted liquid is used as a liniment for diseased skin.

Since the medicine for skin diseases of the present invention is composed of only a natural extract of *Stevia Rebaudiana Bertoni* without any other synthetic chemical additives, it is free of any harmful side-effect with endermic absorption thereof. Where the medicine is externally applied to the diseased skin, it displays an excellent blood circulation promoting effect and attains an improved effect in treating skin diseases.

The medicine of the present invention has been confirmed to be effective against the following skin diseases.

For external application:

Skin burn, scald, acne, heat rash, poisoned skin, eczema, contact-type dermatitis, chilblains, frostbite, inflammation, and chap.

The following examples are intended to illustrate the present invention in more detail but not to restrict it in any way.

EXAMPLE 1

Ripened plants of *Stevia Rebaudiana Bertoni* were harvested at the beginning of November and dried with a tobacco drier having an area of 6.6 m$^2$, with hot air of 75°±3° C. for 24 hours, the air blowing amount being 30 m$^3$/min.

Next, the dried plants were lightly beaten with rods whereby the stems were isolated from the leaves, branches and other impurities. The thus isolated stems were collected.

The stems were cut with a cutter into small pieces of about 3 to 5 cm, then ground two times with a grinder (by Hitachi), and sieved into a fine powder having a mean grain size of 5 μm.

Next, 6 liters of water were put in an iron cauldron and heated, heating was discontinued when the water in the cauldron started to boil, one kg of the above-mentioned fine powder of stems of *Stevia Rebaudiana Bertoni* was gently added thereto, and heating was implemented again for one hour with stirring so that the content was boiled down.

The thus boiled down content was then squeezed with a Nishikawa Model squeezer, whereby the condensed extract was separated from the squeezed refuse. The amount of the first condensed liquid was about 4 liters, and the liquid was put into a tank (condensing cauldron).

Next, 4 liters of water was put in the above-mentioned iron cauldron and heated, heating was mentioned squeezed refuse was gently put thereinto, and heating was implemented again for about one hour with stirring until the content was boiled down. This was then squeezed with the above mentioned squeezer, whereby the condensed extract was separated from the squeezed refuse. The amount of the second concentrated liquid was about 3 liters, and the liquid was added to the above-mentioned tank (condensing cauldron) already containing the above-mentioned first concentrated liquid, and the two were mixed therein.

Next, the mixed liquid in the tank was boiled down to obtain a condensed mixture of liquid of about 500 cc in about 4 hours. The condensed liquid was then filtered through a cotton bag, and the resulting filtrate was put into a stainless steel storage tank and fermented and ripened therein at 25° C. for 360 days.

Accordingly, a medicine for skin diseases of the present invention was obtained, which was an extremely low viscous and brownish green liquid having a sweet aroma.

The following examples demonstrate use of the thus fermented and ripened extract of the present invention as a medicine for skin diseases.

| Sex | Age | Condition | Application Method of the Medicine of the Present Invention | Result |
|---|---|---|---|---|
| female | 18 | acne | add 3 to 4 drops of the medicine to water and wash the face with the water | 10 Days after, acne began to disappear, and on day 15, was almost gone. |
| male | 3 | heat rash (itching) | add 3 to 4 drops of the medicine to water and apply to the diseased part (4 times a day) | 3 Days after, itching was lightened, and 5 days after, the heat rash disappeared. |
| male | 48 | poisoned by ginkgo nuts (severe itching) | apply in a non-diluted form | Itching sensation disappeared in several minutes. |
| male | 37 | scald | apply in a non-diluted form | The pain disappeared in a few minutes, and the inflamed part healed after 5 days. |

In accordance with the present invention, there are provided a medicine for skin diseases, which has the pharmaceutical effects of healing various disease symptoms and promoting blood circulation for various skin diseases and other diseases caused by blood circulation insufficiency, such as stiff shoulders, neuralgia, anemia with oversensitivity to cold, lumbago, rheumatism, chapped skin, heat rash, eczema, acne, bruise, inflammation, chilblains, frostbite, poisoned skin, itch, atopic dermatitis and others, the medicine containing only a fermented and condensed extract from stems of *Stevia Rebaudiana Bertoni*.

The medicine of the present invention may easily be prepared by grinding stems of *Stevia Rebaudiana Bertoni*, extracting the ground powder, condensing the resulting extract by multi-stage condensation, and finally fermenting and ripening the condensed extract.

While the invention has been described in detail and with reference to specific embodiments thereof, it will be apparent to one skilled in the art that various changes and modifications can be made therein without departing from the spirit and scope thereof.

What is claimed is:

1. A medicine comprising a concentrated and fermented extract from stems of matured *Stevia Rebaudiana Bertoni*.

2. A medicine comprising an extract from *Stevia Rebaudiana Bertoni* obtained by the process of:
condensing stems of matured *Stevia Rebaudiana Bertoni* by boiling said stems to obtain a concentrated liquid extract, and
fermenting said concentrated liquid extract.

3. A medicine as in claim 2, wherein said fermenting is effected at 15° C. to 25° C. for from 90 to 360 days.

4. A medicine as in claim 2, wherein said condensing comprises boiling stems of matured *Stevia Rebaudiana Bertoni* to obtain a first concentrated liquid extract and a residue, and separating said first concentrated liquid extract and said residue.

5. A medicine as in claim 4, further comprising condensing said separated residue by boiling said residue to obtain a second concentrated liquid extract and a second residue, separating said second concentrated liquid extract and said second residue, and combining said first and second concentrated liquid extracts before fermenting.

6. A process for preparing a medicine, comprising condensing stems of matured *Stevia Rebaudiana Bertoni* by boiling said stems to obtain a concentrated liquid extract, and then fermenting said concentrated liquid extract to obtain a ripened natural extract as said medicine.

7. A process as in claim 6, wherein said condensation comprises boiling stems of matured *Stevia Rebaudiana Bertoni* to obtain a first concentrated liquid extract and a residue, and separating said first concentrated liquid extract and said residue.

8. A process as in claim 7, further comprising condensing said separated residue by boiling said residue to obtain a second concentrated liquid extract and a second residue, separating said second concentrated liquid extract and said second residue, and combining said first and second concentrated liquid extracts before fermenting.

9. A process as in claim 6, wherein said fermenting is effected at 15° C. to 25° C. for from 90 to 360 days.

10. A process as in claim 6, further comprising to boiling, drying stems of matured *Stevia Rebaudiana Bertoni*, and powdering said dried stems to a size of 15 μm or less.

11. A process as in claim 10, wherein said drying is effected at about 70° to 80° C. for 24 hours, and said dried stems are powdered to a size of about 1 to 8 μm.

12. A method for treating skin diseases by promoting blood circulation in the skin, comprising topically applying to skin of a host afflicted with a skin disease, an effective amount of a topical medicine comprising a fermented and concentrated extract from stems of matured *Stevia Rebaudiana Bertoni*.

13. A method as in claim 12, wherein sad topical medicine is an aqueous solution of said extract.

* * * * *